Figure 1:
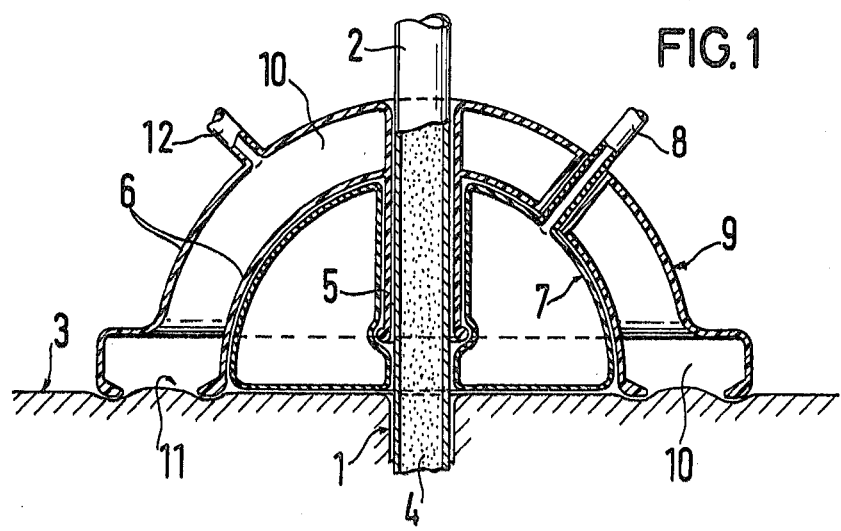

United States Patent [19]

Weigand

[11] 4,096,853
[45] Jun. 27, 1978

[54] DEVICE FOR THE INTRODUCTION OF CONTRAST MEDIUM INTO AN ANUS PRAETER

[75] Inventor: Hanfried Weigand, Mainz, Germany

[73] Assignee: Hoechst Aktiengesellschaft, Frankfurt am Main, Germany

[21] Appl. No.: 696,404

[22] Filed: Jun. 15, 1976

[30] Foreign Application Priority Data

Jun. 21, 1975 Germany .................... 2527706

[51] Int. Cl.² ............................................ A61M 3/00
[52] U.S. Cl. .................................. 128/2 A; 128/245; 128/246; 128/348
[58] Field of Search ............ 128/2 A, 2 R, 1 R, 239, 128/246, 348, 349, 245

[56] References Cited

U.S. PATENT DOCUMENTS

| 90,217 | 5/1869 | Aylworth | 128/246 UX |
|---|---|---|---|
| 2,865,373 | 12/1958 | Recker | 128/239 |
| 2,898,917 | 8/1959 | Wallace | 128/350 R |
| 3,487,837 | 1/1970 | Petersen | 128/349 R |
| 3,543,744 | 12/1970 | Le Par | 128/2 A |
| 3,577,982 | 5/1971 | Le Par | 128/2 A |
| 3,581,732 | 6/1971 | Ruiz | 128/2 A |
| 3,765,413 | 10/1973 | Le Par | 128/245 |
| 3,893,446 | 7/1975 | Miller | 128/2 A |
| 3,970,089 | 7/1976 | Saice | 128/348 |

Primary Examiner—Kyle L. Howell
Attorney, Agent, or Firm—Curtis, Morris & Safford

[57] ABSTRACT

A device for the introduction of contrast medium into an anus praeter shaped in the abdominal wall using an inlet pipe to be inserted into the anus, which comprises an inlet pipe surrounded by a bell-shaped device that is open toward the abdominal wall and rests, at its circumference with a circular ring contact area, against the abdominal wall and with a circular bladder in its interior, that also rests against the abdominal wall in the area between the contact area and the inlet pipe and which is capable of being put under excess pressure.

10 Claims, 5 Drawing Figures

DEVICE FOR THE INTRODUCTION OF CONTRAST MEDIUM INTO AN ANUS PRAETER

The present invention relates to a device suitable for introducing a contrast medium into an anus praeter or artificial anus placed in the abdominal wall, using an inlet tube to be inserted in the anus praeter.

For an X-ray examination of the intestine, especially of the large intestine, the intestine has to be filled with a contrast medium of relatively high viscosity so as to opacify even small cavities in the intestinal wall and give as complete as possible an X-ray picture of all the details of the intestinal wall.

Liquid contrast medium is introduced into the natural anus using an inlet pipe that may be surrounded at its lower end with a ring-shaped inflatable balloon, provided the sphincter is not entirely sufficient. In the contact area of this balloon, the anal sphincter supports the intestinal wall so as to offer enough resistance for the balloon to produce the desired sealing effect.

Those known measures are, however, not adequate for the introduction of contrast medium into an artifical anus (anus praeter), due to the lack of a sphincter which could support a circular ring shaped balloon inflatable in the anus. Moreover, the introduction of such a balloon would require leaving the last portion of the intestine immediately prior to the anus praeter empty of contrast medium, thus excluding it from X-ray examination, although this part may especially be exposed to danger and therefore liable to close inspection. The same is true in the case where inadvertent escape of contrast medium near the artificial anus is to be prevented by pushing the inlet pipe into the anus as far as possible, which additionally might cause inconvenience and pains to the patient.

Up to now, therefore, attempts to introduce contrast medium into an anus praeter result, in many cases, in an escape of large amount of this contrast medium. This is the more unsatisfactory as just the patients having an artificial anus have to be subjected to particularly frequent and careful X-ray examinations as a result of a carcinoma that has required the operation of the intestine and the opening of an artificial anus.

This invention now provides a device for the introduction of contrast medium of the above-said type, which safely prevents the contrast medium escaping from an artificial anus (anus praeter) in the colon contrast medium method. In this connection, the entire and never overlapping intestine, especially its last portion, is to be filled with contrast medium to guarantee complete X-ray examination.

The problem of the invention is solved by means of an inlet pipe that is surrounded by a bell-shaped device which rests with its open, circular ring base against the abdominal wall and has, in its interior, a circular bladder capable of being put under excess pressure and resting against the abdominal wall in the area between the contact base of the bell and the inlet pipe.

The contact base ensures a tight hold of the device on the abdominal wall at a certain distance to the anus praeter. There is no force acting between the inlet pipe and the anus to achieve a sealing effect so that painful deformation of the anus having no sphincter is avoided. The circular bladder to be put under excess pressure fits, in a relatively broad circular area, thightly to the abdominal wall and prevents the contrast medium from escaping even at sudden movements and/or muscular tensions of the patient.

In one embodiment of this invention, the inlet pipe is positioned in a central tube of the bell-shaped device and the circular bladder embraces the inlet pipe at least in its lower portion near the anus. This allows the inlet pipe to be shaped as a displaceable arrangement with regard to the "bell", that can be brought into adequate position. Within the central pipe, there is no contact between the circular bladder and the inlet pipe but the bladder embraces the inlet pipe immediately above the anus to seal it and prevent the escaping contrast medium from running along the pipe.

In another embodiment of the invention, the contact base is formed by two concentric brims of the "bell", between which there is a circular suction aperture capable of being put under reduced pressure. This allows the bell to be sucked tight onto the abdominal wall using the adequate adhesion force required before putting excess pressure onto the circular bladder. The suction force used for each case may be as high as to exceed the pressing force produced by the bladder, at an always sufficient degree. If required, relatively high pressure may thus also be applied by means of the bladder.

The contact base surface may also be formed by a double-face adhesive strip fixed to a circular ring surface at the circumference of the bell. This constitutes a particularly simple embodiment of the bell, which may therefore be intended for single use only, at relatively low cost.

In still another embodiment of this invention, the contact surface base may instead also be formed by a circumferential bulge of the bell which may additionally be tightened to the abdominal wall by means of a belly strap attachable to the bell. This embodiment also has a very simple construction.

In a slightly modified embodiment, the adhering effect to the abdominal wall may be improved using, as the contact base, the concentrically grooved ring surface of a rubber-elastic ring fixed to the bell and additionally, a belly strap which, in this embodiment, has to exert only moderate pressure.

The device of this invention is illustrated diagrammatically by way of example in the attached drawings. In these drawings, FIG. 1 is a vertical, cross-sectional view of a device with a double-wall bell and a circular suction aperture.

Figure 2:
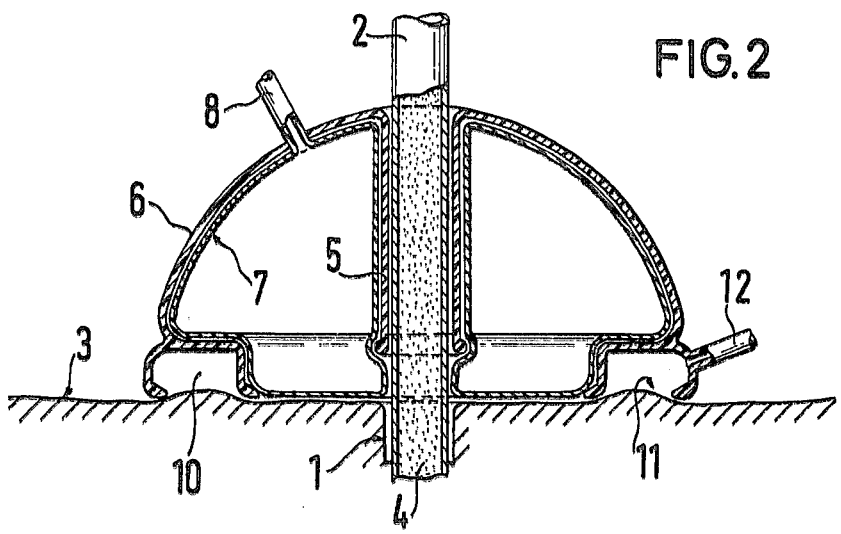
Figure 3:
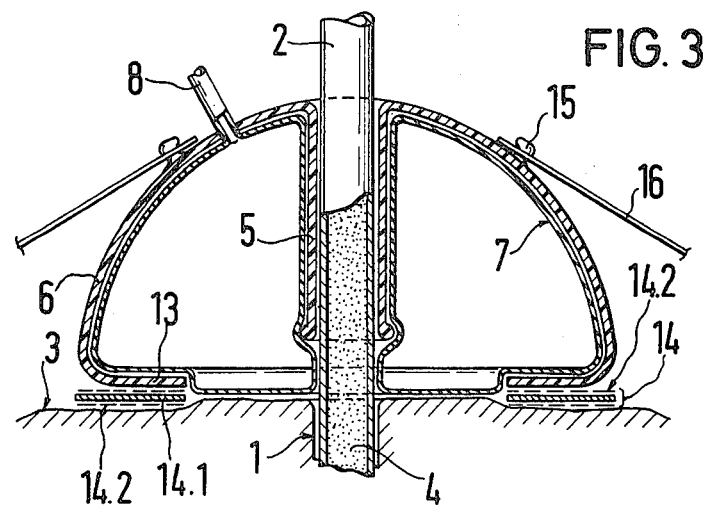
Figure 4:
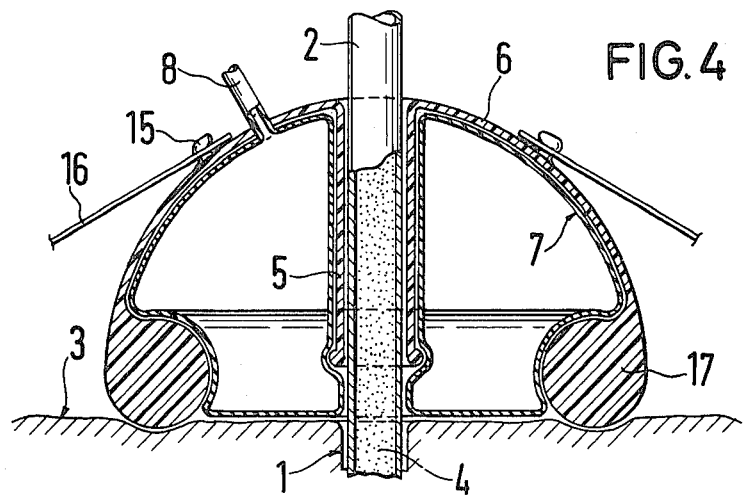
Figure 5:
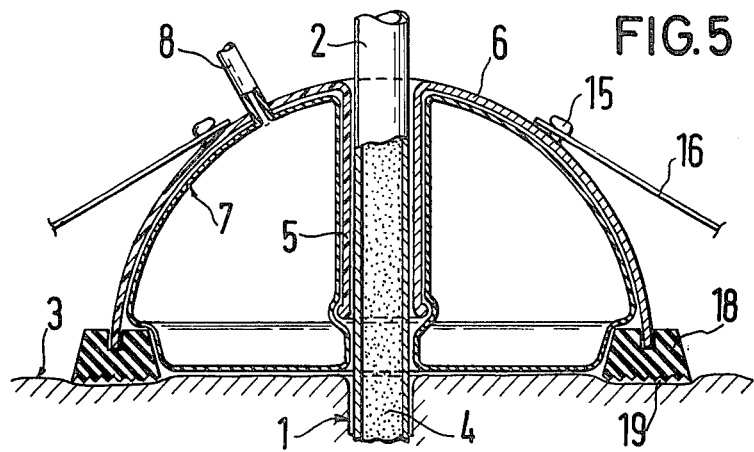

FIG. 2 is a vertical cross-sectional view of a device in which the circular suction aperture is shaped as a lower hollow ring attached to the bell, FIG. 3 is a vertical, cross-sectional view of a device with a double-face, adhesive strip, FIG. 4 is a vertical, cross-sectional view of the device provided with a bottom circumferential bulge fixed to the bell, and FIG. 5 is a vertical, cross-sectional view of the device provided with a rubber-elastic ring equipped with adhering grooves.

In these figures the devices for introducing contrast medium into an artificial anus 1 comprise an inlet pipe 2 which is inserted in the anus praeter 1 surgically shaped into abdominal wall 3. A highly viscous contrast medium 4 is introduced through the pipe for the purpose of colon contrast medium diagnosis. The inlet pipe 2 is positioned, in a displaceable manner, in a central pipe 5 that ends with a bulge immediately above the anus 1. The central pipe 5 forms the middle portion of a bell-shaped shell 6, which may be made of plastic material as is the pipe 5 and may be connected with it in conventional manner by welding, bonding or the like, or both may be made in one piece. The bell-shaped shell 6 is of essentially hemispherical shape but may also take various other shapes, for example that of a shallow dish.

The circular cavity between abdominal wall 3 and bell 6, which is penetrated centrically by the pipes 2 and 5, houses a circular bladder 7 made of rubber, plastics or similar material, which can be filled with a compressed medium, for example air, and put under excess pressure by means of an outward conduct 8. The bladder 7 rests, with a relatively broad circular ring area, against the abdominal wall 3 and also embraces the inlet pipe 2 tightly in the area immediately above the anus 1. When the bell 6 is retained on the abdominal wall by measures specified in the following, and the bladder 7 has been inflated, they apply tightly to the abdominal wall and to the inlet pipe 2, sealing them both off, so that the contrast medium 4 can be introduced into the intestine without escaping therefrom.

The difference between the embodiments illustrated in FIGS. 1 to 5 are primarily in how to retain bell 6 on abdominal wall 3.

In FIG. 1 the bell 3 has an outer shell 9. Bell 6 and outer shell 9 have between them a hollow space 10 which enlarges at the lower brim of the bell to form a circular ring-shaped suction aperture 11. When the air is sucked off the hollow space 10 through a conduit 12, connected with hollow space 10, the bell 6 becomes attached by suction with its circular ring area 11 to the abdominal wall 3.

In FIG. 2, the embodiment also has a circular ring suction area 11 which, however, is the outlet of a smaller circular hollow ring 10 in which the pressure can be reduced by means of a conduit 12. The devices, for example pumps, suitable for generating excess pressure in the bladder 7 and reduced pressure in the hollow space 10 are not shown in the figures for simplicity's sake, as they are of conventional types.

In FIG. 3 the lower brim of the bell 6, which ends in an inward-reaching, optionally reinforced, flange 13, is provided with a double-face adhesive strip 14. This strip consists of a core strip 14.1 and upper and lower adhesive layers 14.2, which are shown in broken lines in the FIG. 3. If this device is to be used several times, the adhesive strip 14 may be pulled off after use and replaced by a new one. Should the adhesive power of strip 14 not, or not safely, be sufficient, the bell 6 may additionally be pressed onto the abdominal wall 3 by means of a belly strap 16 fixed to hooks 15.

In the embodiments shown in FIGS. 4 and 5, the belly strap 16 serves primarily to attach the bell 6 to the abdominal wall 3. In FIG. 4, the lower brim of bell 6 ends in a circular cirumferential bead 17 which is pressed against the abdominal wall 3.

In FIG. 5 the lower brim of bell 6 is fitted into a rubber-elastic ring 18, the bottom face of which, forming the contact area, is a circular surface provided with concentric grooves 19.

The material used has largely to be permeable to X-rays in order not to invonvenience or impair the examinations.

Adhesion of bell 6 to the abdominal wall may also be brought about by implanting, underneath the skin, a circular magnet which will be attracted by a corresponding ring attached to the lower brim of bell 6.

What is claimed is:

1. A device for the introduction of a contrast medium into an anus praeter formed in an abdominal wall comprising an inlet pipe adapted to be inserted into said anus praeter, a housing having an open end, said housing surrounding said inlet pipe and having an abdominal contact area surrounding said open end, the housing being adapted to be positioned with said contact area against said abdominal wall with its open end facing the wall when said inlet pipe is in said anus praeter, and an inflatable bladder contained within said housing separate from and surrounding said inlet pipe, said bladder having at least one flat surface defining an abdominal wall contact surface surrounding said inlet pipe and extending radially therefrom for contacting the surface of said abdominal wall surrounding said anus praeter when the bladder is inflated, and means for holding said contact area of the housing against said abdominal wall, thereby to hold said flat surface of said bladder against the abdominal wall and form a seat therewith while the inflated bladder holds said inlet pipe against longitudinal movement.

2. A device as defined in claim 1 wherein said contact area of the housing and the flat surface of the bladder are each circular.

3. A device as defined in claim 2 wherein said housing is generally semi-spherical in shape.

4. A device as defined in claim 3 wherein said bladder is generally semi-spherical in shape and complementary to said housing, said bladder having a central passage therein receiving said inlet pipe.

5. A device as defined in claim 4, wherein the circular bladder embraces the inlet pipe at least in its lower portion near the anus praeter.

6. A device as claimed in claim 4, wherein the contact area of the housing includes two concentric brims defining between them a circular ring suction aperture adapted to be placed under reduced pressure to define said holding means.

7. A device as defined in claim 4, wherein said holding means comprises a double-faced adhesive strip attached to said circular contact area at the circumference of the bell.

8. A device as claimed in claim 4, wherein the contact area is shaped as a circumference bead of the housing, and said holding means comprises a belly strap attached to the housing adapted to press it onto the abdominal wall.

9. A device as claimed in claim 4, wherein the contact area is a concentrically grooved ring surface formed of a rubber-elastic ring attached to the housing, and a bell strap attached to the housing adapted to press it onto the abdominal wall.

10. A device as claimed in claim 4, wherein the contact area of the housing includes circular magnet adapted to match a corresponding magnet implanted in the abdominal wall around the anus praeter.

* * * * *